United States Patent [19]

Markhart, III

[11] Patent Number: 4,713,344
[45] Date of Patent: Dec. 15, 1987

[54] HAND OPERATED PRESS FOR TISSUE EXTRACTION

[75] Inventor: Albert H. Markhart, III, St. Paul, Minn.

[73] Assignee: Regents of the University of Minnesota, Minneapolis, Minn.

[21] Appl. No.: 629,584

[22] Filed: Jul. 11, 1984

[51] Int. Cl.[4] .............................................. C12M 1/00
[52] U.S. Cl. ................................... 435/287; 435/310; 435/30; 210/314
[58] Field of Search ................ 435/287, 311, 302, 30; 210/927, 314, 323.2, 322, 338, 324, 359, 155, 166, 789, 964, 298, 357, 773, 516, 767; 241/95, 169.2

[56] References Cited

U.S. PATENT DOCUMENTS

| | | | |
|---|---|---|---|
| 2,879,207 | 3/1959 | Poitras | 435/311 |
| 3,448,011 | 6/1969 | Russomanno | 435/287 |
| 3,720,583 | 3/1973 | Fister | 435/302 |
| 4,021,352 | 5/1977 | Sanstedt | 210/789 |
| 4,092,221 | 5/1978 | Schlichting, Jr. | 435/311 |
| 4,092,246 | 5/1978 | Kummer | 210/767 |
| 4,413,059 | 11/1983 | Tihon et al. | 435/311 |
| 4,435,505 | 3/1984 | Zierat | 435/311 |
| 4,454,032 | 6/1984 | DuPont et al. | 210/324 |

FOREIGN PATENT DOCUMENTS 8207121  3/1982  Fed. Rep. of Germany ...... 435/287

OTHER PUBLICATIONS

Broyer, T. C., A. H. Furnstal, *A Press for Recovery of Fluids from Plant Tissues,* 1941, vol. 16, pp. 419–421.
Screenivasaya, et al., *Micropress for Obtaining Press Sap from Plant Tissues,* Apr., 1967, vol. 5.
Susplugas, J., et al, *Technique D'Obtention Des Scus Vegtaux,* in Methodology of Plant Eco-physiology, 1965, pp. 393–397.

*Primary Examiner*—Samuel Scott
*Assistant Examiner*—H. A. Oda
*Attorney, Agent, or Firm*—Kinney & Lange

[57] ABSTRACT

A hand operated press is used for extracting cell sap from biological tissue, such as from leaf tissue of plants, as well as from animal tissue as a removable barrel that holds a suitable screen in place in a well. The barrel houses a plunger that is of small diameter so that when the barrel has tissue added to it the plunger is inserted and a substantial pressure may be exerted manually to insure rupturing the cell membranes and releasing all of the cell liquid (in plants called sap) for analysis. In the preferred form the screen holds at least one standard size filter paper disk in place so that the liquid is first forced through the screen to retain large solid particles, and the filter paper disk is wetted for use in a standard analyzer for direct analysis of the desired characteristics. The press is portable, easy to use and disassemble for cleaning, and reduces the time required for determining characteristics of a cell, such as its osmotic potential, and also reduces the chance of the sap becoming altered by environmental factors.

12 Claims, 2 Drawing Figures

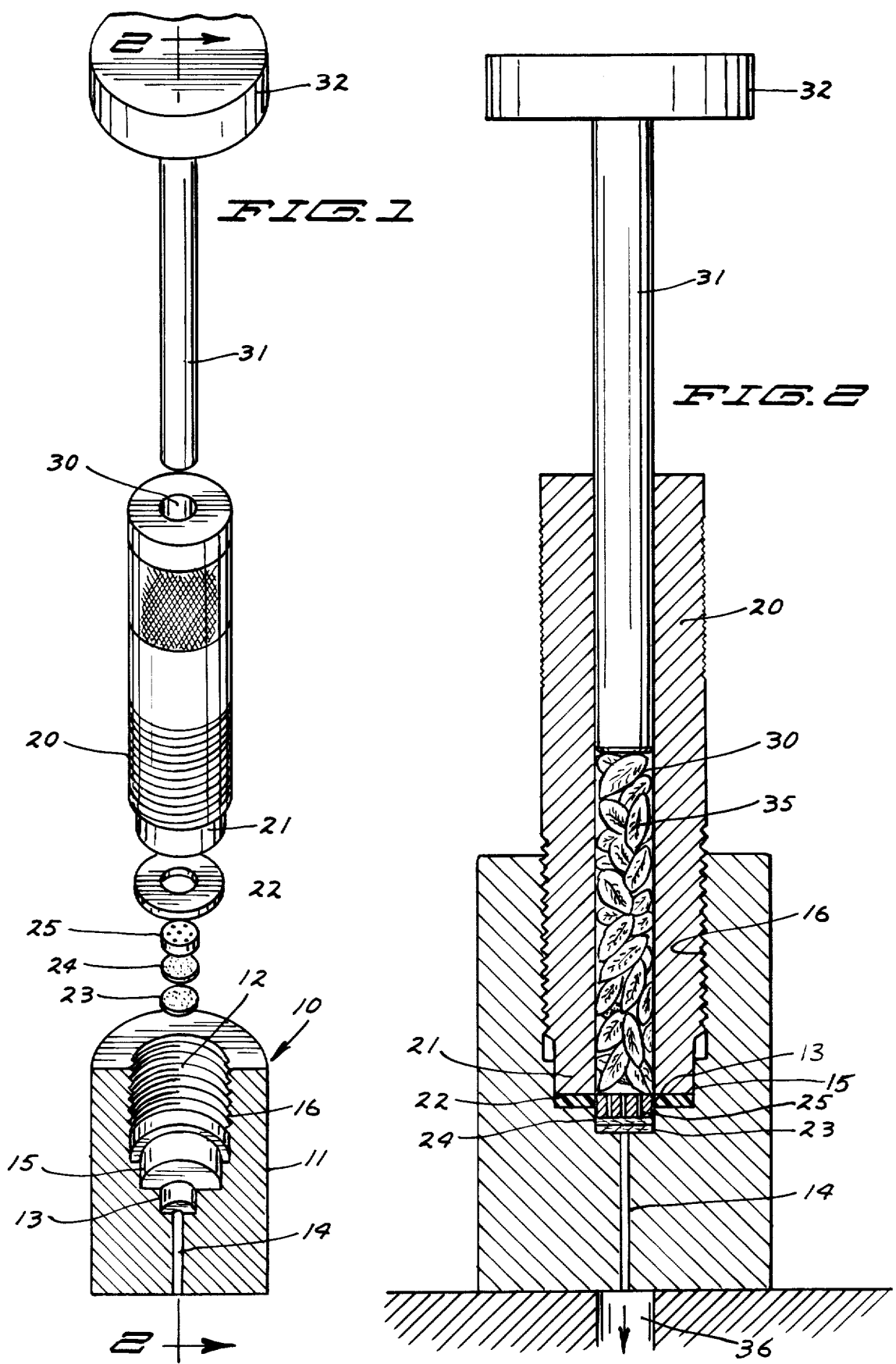

HAND OPERATED PRESS FOR TISSUE EXTRACTION

BACKGROUND OF THE INVENTION

1. Field of the Invention

The present invention relates to manually operated presses for use in analyzing characteristics of the liquid content of biological cells.

2. Description of the Prior Art

It has long been desired to obtain the sap from the cells of plant tissues in particular, using various methods. Small hand operated presses have been used. For example, a Micropress Assembly having a base and a fixed barrel with an outlet into which a plunger can be inserted for attempting to squeeze liquid material from tissue is shown in an article entitled *Micropress for Obtaining Press Sap from Plant Tissues* by Sreenivasaya et al. in Indian Journal of Experimental Biology, Vol. 5, (April 1967).

Another type of press which is hand operated and moves in a barrel for forcing liquid from plant tissue is shown in a paper entitled *A Press for Recovery of Fluids from Plant Tissues* by Broyer in Plant Physiology, Vol. 16 pp 419–421 (1941). This device shows a type of a sieve plate at the bottom of the chamber, but the press is quite large in diameter, and has a chamber at the bottom through which sap can be expressed. This device is specifically designed for operation with a screw type press or a hydraulic cylinder press and it is not intended to be hand operated. In other words, the device is of substantial size and requires substantial force to operate.

Another type of press that has a fairly large piston (5 centimeters) is shown in an article entitled *Technique D'Obtention Des Sucs Vegetaux* by J. Susplugas, et al. in Methodology of Plant Eco-physiology, pages 393–397 (1965).

However rapidly used, reliable presses which are portable and adapted to existing analysis equipment have not been available. The need for analysis of cell sap or other liquids from biological cells continues to exist in order to study cell and plant characteristics, and to obtain favorable characteristics in future generations of plants and animals.

The osmotic potential of plant tissues is an important component of the overall water relations of the plant. As is seen in equation 1 the water potential ($\gamma w$) of a cell is equal to the osmotic potential ($\gamma s$) plus the turgor potential ($\gamma p$).

$$\gamma w = \gamma s + \gamma p \tag{1}$$

Equation 1 can be rearranged to show that the turgor potential of the tissue is proportional to the osmotic potential at a constant water potential (eq. 2).

$$\gamma p \alpha \gamma s^* (\text{constant } \gamma w) \tag{2}$$

The osmotic potential therefore is extremely important in determining the turgor of the leaf. The lower the osmotic potential, the lower the water potential the plant can reach and still have positive turgor. The point of zero turgor has been associated with wilting, decreased photosynthesis, and reduced growth in many plant species. Recently it has been observed that many plant species show changes in osmotic potential when exposed to periods of water stress. These observations suggest that the maintenance of a positive turgor in plants is an important adaptation to growth under drought conditions.

Although there are excellent instruments available for determining the osmotic potential of solutions, there remain considerable problems in accurately measuring the osmotic potential of bulk tissue. The limitations are due primarily to inadequate methods of extraction of sap from tissue cells and subsequent transfer of the sap to the measuring instrument without changes in concentration.

The osmotic potential of the sap is presently carried out with very reliable instruments that can measure the osmotic potential of the plant cell with small amounts of cell sap, sufficient only to wet a small filter paper. In order to obtain cell sap, the cell membranes (the lining just inside the cell wall) have to be ruptured. One method that is commonly used to rupture the cell membranes is to freeze the tissue and then thaw it again. The expanding ice crystals upon freezing pierce the cell membrane and the cell walls, eliminating any cell tugor, which is the rigidity or turgidity of the cell. The thawed piece of leaf tissue is then placed in a thermocouple psychrometer (a conventional instrument) and the water potential of the dead tissue is measured.

A second method for obtaining cell sap is to place the tissue in a cylinder with a mesh covered hole at one end, much like the pressures shown in the previously described prior art, and then compressing the tissue by a plunger moving down the cylinder barrel. This generally requires a large press with existing equipment, and the resulting leaf sap is forced out a small hole in the end of the barrel and collected for future analysis. Large pieces of cell material that pass through the screen are removed by either centrifugation or filtration, and then the remaining solution is tested in an osmometer for water potential.

In the first method, after the sample has been put into a thermocouple instrument, an equilibrium time of at least two hours is needed before an accurate measurement can be obtained. This requires that a large number of thermocouple points be used. Twelve to Twenty Four such points are required for adequate replication. Each point requires its own calibration procedure which requires five solutions of known osmotic potential.

During the length of time needed for insuring that equilibrium conditions have been established, there is ample opportunity for enzyme action to degrade the tissue components causing a change in the osmotic potential of the sap being tested. Recent studies have shown that such degradation does occur.

The second method described, which uses a vapor pressure osmometer for measuring the osmotic potential of the extracted solution, has the advantage of easy calibration and a very small sample size. Equilibrium time is extremely rapid, and the measurement can be completed in only ninety seconds. The limitations of using this method, however, lie in the sap extraction procedure. One disadvantage of a conventional cylinder (press) extraction is that changes can occur in the osmotic potential of the expressed cell sap between extraction and measurement. Any exposure of the sap to the atmosphere allows evaporation of water and a change of the osmotic potential of the sap. Centrifuging and filtering both require time and can result in changes in the osmotic potential of the sap. The procedure is time consuming and thus tedious.

SUMMARY OF THE INVENTION

The present invention relates to an apparatus for expressing or pressing cell liquids, commonly called cell sap, from biological tissue. The apparatus is used in a process which provides for directly using the expressed sap in conventional instrumentation for determining characteristics of scientific interest such as the water potential of the cell, which in turn provides information relating to cell functions such as its ability to withstand stress from insufficient water. Analyzation of sap for other characteristics, such as ion and carbohydrate content, and also nitrogen determinations can be made from the cell sap.

In relation to plant tissue, the determination of the osmotic potential is helpful in determining the ability of particular plants to withstand drought conditions. The lower the osmotic potential, the better the plant will withstand drought. The turgor (a measure of rigidity) of a cell is an important factor. Once the turgor of a cell goes to zero, the plant wilts and function is impaired.

In analyzing liquid content from cells it is important that the process used insures that the membrane lining on the interior of each of the cell walls is ruptured. The membrane is a semi-permeable barrier that controls ion exchange and passage of water into and out of interior of the cell. As stated, in prior methods, freezing the cell was required in order for the ice crystals to pierce the membrane, but with the present press, a hand operated plunger will provide sufficiently high pressures to insure rupturing the cell membrane, and the other portions of the press, particularly in the preferred embodiment, the filter papers at the bottom which eliminate the need for separate centrifuging or filtering, will provide an adequate liquid sample from tissue that is intact (not frozen) quickly and reliably.

The press of the present invention is easily dissembled for cleaning and then can quickly be reused. Filter papers are used in the bottom of the well that holds the barrel in the preferred embodiment, but the press can be used for collecting cell sap through an exhaust or discharge passageway, which sap can then be analyzed in any desired way.

A unique process is followed, in particular in connection with a commercially available osmometer that uses a wetted filter paper for analysis of cell sap, and comprises the steps of providing a press that has two filter papers covering a discharge orifice, a screen held in place over the filter paper with a press barrel into which pieces of biological tissue are placed, and a hand operated plunger that slides through the barrel and ruptures the cells from pressure, passing the cell sap through the screen, through the first filter paper and wetting the second filter paper. When the second filter paper becomes satuated to the desired degree the barrel is removed, the screen removed, and the second filter paper is used in analyzing the cell sap for desired characteristics, such as osmotic potential.

Because the press is easily disassembled to remove the filter paper, the total time is significantly reduced, which assures that the cell sap will not be adversely affected by environmental conditions prior to being analyzed. The press is easily cleaned to be ready for the next sample as well.

A significant savings is made in set up time using the present device including a filter paper osmometer as opposed to a thermocouple psychrometer. A saving is made in measurement time because the leaf tissues can be pressed for extracting the sap, the filter paper removed quickly, the liquid tested and then the press cleaned and reused. Ten to twelve samples can easily be measured in an hour with the present device, because it does not require centrifugation or filtration of the sap sample prior to measurement. An increase in accuracy is also obtained because the direct transfer from the site of the disruption of the cell (the small portable hand press) directly to the osmometer reduces the time of exposure of the sample to air, and substantially reduces evaporation or concentration of the cell sap sample. This is extremely important for insuring reproducibility in accurate measurements.

The device of the present invention, in direct comparison tests, has been shown to be well within the reproducibility of results that is necessary for experimental analyzation of cell sap.

Also, in direct comparison with processes involving the freezing of cells, it was shown that the cell membranes of the tissue cells being tested were adequately ruptured and the comparison was favorably made with the existing processes.

The press of the present invention also may be used for obtaining cell liquids from tissue of animals and other creatures. The analysis of such liquids for characteristics of scientific interest may be made from samples contained on the filter paper, just as with plant tissue.

BRIEF DESCRIPTION OF THE DRAWINGS

FIG. 1 is an exploded view of a tissue press made according to the present invention; and FIG. 2 is a vertical sectional view of the press in FIG. 1 showing it in a working position.

DETAILED DESCRIPTION OF THE PREFERRED EMBODIMENTS

In the preferred form, the press is adapted to be used with a vapor pressure osmonitor made by Wescor, Inc., of Logan, Utah, Model 510, which uses a small filter disk of a standard size (outside diameter) that is satuated with cell liquid (sap), and placed into a receptacle and then analyzed. The filter disks are only about 0.5 cm in diameter for use in such an osmometer, and the present press is adapted for operation with these filter disks so that the tissue cells are ruptured, the sap expressed from the cells to wet the filter paper used, and the filter paper can be removed from the press with only the liquid to be analyzed saturating or wetting the filter paper. The filter paper may be inserted in the osmometer (or other instrument) for analyzation very rapidly.

The osmotic potential of sap is a function of the water potential and the turgor potential of a cell. The turgor potential has to do with the turgidity or rigidity of the cell. The water potential is a factor that relates to how much attraction the cell has for water. The turgor potential generally is a positive number, and indicates a tendency to push liquid out of the cell. The water potential is a negative number and is a function of the tendency to attract water into the cell. When the cell reaches zero turgor it wilts.

The press of the present invention, which is used for extracting cell sap or liquid, is shown at 10 in FIG. 1. It includes a housing support or well 11, which has an interior opening indicated at 12 therein. A subchamber 13 is formed at the interior end of opening 12. In the preferred form of the invention, the subchamber is only 0.5 cm in diameter, and has a flat bottom surface. A small discharge passageway 14 opens through the bottom surface of the housing or well 11 into the subchamber 13. Above the subchamber 13, there is a counterbore chamber 15, and above that a slightly larger threaded section 16. The threaded section is made to receive the external threads of a press barrel 20. The press barrel 20 has a neck 21 which will fit into the counterbore 15, and the barrel will thread into the threaded portion 16 against a seal washer 22 that fits into the counterbore. The barrel also retains a first filter paper disk 23, a second filter paper disk 24, and a screen member 25 in place in the subchamber 13 in the form shown.

The screen member 25 comprises a perforated metal cylinder that fits closely into the well subchamber 13. The filter disks 23 and 24 also fit snugly into this subchamber. The washer 22 has the same internal diameter as the diameter of the subchamber and of the filter disks and screen 25. The end portion 21 of the barrel 20 fits tightly against the washer 22, which may be made of a suitable material such as Teflon for example. When the barrel is threaded into place it will clamp the washer in place to form a seal around the screen 25.

The barrel has a press bore 30 defined therethrough which is co-axial with the subchamber 13, and with the passageway 14. The bore 20 is of size to closely and snugly receive a press plunger 31 and is a manually operated plunger having a hand head 32 at an outer end thereof. The barrel itself is substantially longer than the outside diameter, and in the form shown, the barrel would be approximately 6.5 cm. long with an outside diameter of 2.0 cm. and an inside diameter of 0.6 cm. The diameter of the bore 30 is thus just slightly larger than the diameter of the screen 25 and the subchamber 13.

Biological tissue indicated generally at 25 is placed into the bore 30 after the unit is assembled as shown in FIG. 2. The bore 30 can be filled to any desired level. The tissue generally is cut or broken into pieces so that it can be placed into the bore. The plunger 31 then is placed in position in the bore 20 and the head 32 is pushed manually, with force sufficient to rupture the cell membranes and press cell sap out of the tissue. Rupturing the cell membrane is critical to obtain satisfactory results. Two features contribute to the ability to accomplish the requirements. The first is having a small diameter plunger which permits high pressure (kg/cm$^2$) and secondly the use of small, standard size filter disks, which do not require a large liquid volume to wet them.

The cell sap will be forced downwardly through the screen 25 as the tissue is compressed and then through the first and second layers of filter paper 23 and 24. Disk 24 filters out debris that might pass through the passageways in the screen 25, and the filter paper 23 then receives cell sap with no debris, and holds a representative sample of cell sap from the tissue 35 with no adverse effects from environmental conditions. The screen has axial length sufficient to be rigid and not bend or bow out of shape. This also insures that the filter disks remain properly positioned.

After the plunger 31 has been pressed into position to extract all of the sap, it is withdrawn and the barrel is then unscrewed and removed from the well. The screen 25 and teflon washer 22 can be removed, and the upper filter disk 24 is removed. The first filter disk 23 is then immediately placed into the osmometer and analyzed. It has cell sap that has not been subjected to detrimental environmental conditions, and provides a true reading of the characteristics of such sap.

This is done very rapidly because the barrel can be unscrewed quickly, and the filter paper retrieved.

Where filter paper is not used, the bore 14 (which will discharge any excess sap) may be used for discharging the liquid into a passageway 36 leading to a suitable receptacle if desired, and while only relatively small samples are handled, the cell sap can be collected for analyzation in any type of analyzer desired.

The small diameter of the end of the plunger 31 provides a relatively high pressure capability even when the plunger is manually pressed down. Keeping the bore small and relatively long therefore provides for an easily used press that will provide adequate pressures for rupturing the cell membrane.

The disassembly and assembly of the press also aids in this operation for ease of cleaning, and ease of removal of the filter papers that are used for collecting the sap in the preferred embodiment.

Although the present invention has been described with reference to preferred embodiments, workers skilled in the art will recognize that changes may be made in form and detail without departing from the spirit and scope of the invention.

What is claimed is:

1. A press assembly for extracting and collecting usable samples of liquids from the cells of biological tissue for analysis comprising a housing, a chamber defined in said housing, said chamber having a central axis and an input end for receiving tissue to be pressed and including a subchamber section at an end of said housing opposite from the input end, the subchamber section having an end surface, a discharge passageway having a cross section size substantially smaller than the end surface, the discharge passageway being open through the end surface, and a pair of filter discs of substantially the same size as the end surface supported on the end surface, one on top of the other;

a screen member supported on the filter discs in the subchamber leading from said subchamber;

a barrel member threadably mounted in said housing, said barrel member having a bore coaxial with said subchamber and opening to said screen member, said bore being of substantially smaller diameter than the outer size of the barrel and substantially longer than its diameter; and a plunger means slidably mounted in said bore, said plunger member including a head end of size to be useful for gripping by an operator to push the plunger member through the bore and to exert a pressure on material placed in the bore against said screen member, a first of said filter disks being next to the screen member on a side of the screen member opposite the bore for collecting debris passing through said screen member, liquids forced from tissue in the bore by operation of the plunger member passing through the first filter disk for collection on the second filter disk for analysis.

2. The apparatus as specified in claim 1 and an annular seal member in the bore adapted to be engaged by the lower end of said barrel when the barrel is mounted in said chamber of said housing, said housing and barrel being threadably mounted together to permit clamping the seal member in position surrounding the opening leading to said subchamber.

3. The apparatus of claim 1 wherein said screen comprises a cylinder having an axis parallel to the bore, and a plurality of axially extending openings through said cylinder, said cylinder being of sufficient thickness to resist bowing as the plunger is moved in the bore toward the screen.

4. The apparatus as specified in claim 1 wherein said plunger member has a diameter of less than one centimeter.

5. The apparatus as specified in claim 1 wherein said plunger member is of size slightly larger than a standard 0.5 centimeter diameter filter disk.

6. A tissue press for obtaining sap from tissue cells comprising a base, a receptacle formed in said base, said receptacle having an interior subchamber at an inner end thereof of small diameter, and a main chamber having a threaded portion adjacent its outer end;

a counterbore being positioned between the main chamber and subchamber, said counter bore forming a shoulder surface surrounding the subchamber;

a removable seal member supported on the shoulder surface in said counterbore and having a seal central opening;

a cylinder barrel mounted in said chamber, and having an end portion fitting in said counterbore, the end portion bearing against said seal member, said cylinder barrel having an interior axial bore substantially the same diameter as the subchamber;

a screen member adapted to fit into said subchamber at the lower end of said bore, said screen member comprising a metal cylinder having preforations therethrough and aligned with the seal central opening;

a discharge opening leading from the subchamber to the exterior of said base;

a plunger slidably mounted in said bore, said plunger being of sufficiently small diameter to permit manual pressure sufficiently great to extract existing cell sap from biological tissue placed in said bore above said screen member; and a surface defined in said chamber for supporting filter paper means thereon which is positioned between the screen member and the discharge opening.

7. The apparatus as specified in claim 6 and filter paper means below said screen member in said subchamber to collect anf filter materials expressed by said plunger from said tissue.

8. The apparatus as specified in claim 7 wherein the filter paper means comprises a pair of filter paper disks forming two layers positioned below said screen, the filter paper disk farthest from the plunger being satuated with cell sap during operation of said press.

9. A method of pressing cell liquids from biological tissues for analysis comprising the steps of:

providing a press and having a screen at the remote end thereof;

placing a pair of filter papers in the press adjacent said screen, and positioned so that cell sap removed by said press from plant tissue compressed against said screen and will pass through the screen to saturate the filter papers; and disassembling the press and removing the filter paper farthest from the screen for placement into an analytical instrument.

10. The method of claim 9 including the step of manually pushing a plunger through a bore in said press on the opposite side of said screen from said filter papers, said bore being formed in a barrel threadably mounted in a housing and sealed around said screen.

11. A method of preparing a sample of biological tissue liquid for analysis in an instrument utilizing filter papers comprising the steps of:

providing a tissue press having a housing with a subchamber of size to receive and support a pair of filter disks stacked one on top of the other and of size to be usable for direct analysis in an instrument, said chamber having an exhaust passageway adjacent one end thereof;

placing at least first and second filter disks in said subchamber, one on top of the other;

placing a screen overlying said filter disks;

forming a press for extracting cell liquids adjacent said screen so that upon operating the press the biological tissue will be compressed against said screen;

rupturing the cell membranes in said tissue press and permitting cell liquid to pass through said screen and through both of said filter disks;

compressing sufficient biological tissue to provide cell liquid sufficient to wet the second filter disk farthest from the screen; and dissembling the press, removing the screen and the filter disks and placing the filter disk supported farthest from the screen in an instrument to analyze the cell liquid for desired properties.

12. The method of claim 11 wherein the cell liquid is a plant sap and including the further step of analyzing the sap in a vapor pressure osmometer.

* * * * *

UNITED STATES PATENT AND TRADEMARK OFFICE
CERTIFICATE OF CORRECTION

PATENT NO. : 4,713,344

DATED : December 15, 1987

INVENTOR(S) : Albert H. Markhart, III

It is certified that error appears in the above-identified patent and that said Letters Patent is hereby corrected as shown below:

Column 6, line 46, delete "means" and insert --member--.

Signed and Sealed this

Twenty-first Day of June, 1988

Attest:

DONALD J. QUIGG

Attesting Officer

Commissioner of Patents and Trademarks